(12) United States Patent
Ishii et al.

(10) Patent No.: US 6,831,028 B1
(45) Date of Patent: Dec. 14, 2004

(54) ANTIBACTERIAL GLASS AND METHOD FOR PRODUCTION THEREOF

(75) Inventors: Masao Ishii, Tokyo (JP); Kenichi Tanaka, Tokyo (JP)

(73) Assignee: KOA Glass Co., Ltd., Tokyo (JP)

( * ) Notice: Subject to any disclaimer, the term of this patent is extended or adjusted under 35 U.S.C. 154(b) by 97 days.

(21) Appl. No.: 10/257,946

(22) PCT Filed: Sep. 29, 2000

(86) PCT No.: PCT/JP00/06772

§ 371 (c)(1),
(2), (4) Date: Oct. 23, 2002

(87) PCT Pub. No.: WO02/28792

PCT Pub. Date: Apr. 11, 2002

(51) Int. Cl.[7] .......................... C03C 12/00; C03C 8/18; C03C 3/19

(52) U.S. Cl. .......................... 501/33; 501/19; 501/48; 428/406; 428/401

(58) Field of Search .................. 501/45, 47, 19, 501/32, 33; 424/401, 63; 428/372, 406

(56) References Cited

U.S. PATENT DOCUMENTS

| | | | |
|---|---|---|---|
| 4,931,078 A | * | 6/1990 | Yamamoto ................... 504/151 |
| 5,049,139 A | * | 9/1991 | Gilchrist ...................... 604/265 |
| 5,244,731 A | * | 9/1993 | Saito et al. .................. 428/372 |
| 5,290,544 A | * | 3/1994 | Shimono et al. ............... 424/63 |
| 5,766,611 A | * | 6/1998 | Shimono et al. ............. 424/401 |

FOREIGN PATENT DOCUMENTS

| | | | | | |
|---|---|---|---|---|---|
| JP | 62210098 A | * | 9/1987 | ............. | C02F/1/50 |
| JP | 01313531 A | * | 12/1989 | .............. | C08J/5/00 |
| JP | 05271029 A | * | 10/1993 | .......... | A01N/61/00 |
| JP | 06136180 A | * | 5/1994 | ............. | C08K/3/40 |
| JP | 07048539 A | * | 2/1995 | ......... | C09D/133/14 |
| JP | 08048539 A | * | 2/1996 | .............. | C03C/4/00 |
| JP | 08245240 A | * | 9/1996 | ........... | C03C/12/00 |
| JP | 09110453 A | * | 4/1997 | ......... | C03B/37/005 |
| JP | 2000191339 A | * | 7/2000 | .............. | C03C/3/17 |

OTHER PUBLICATIONS

Machine translation of JP 08–245240.*
Machine translation of JP 05–271029.*
Derwent Abstract 1993–365103 of JP 05–271029.*

* cited by examiner

*Primary Examiner*—Karl Group
*Assistant Examiner*—Elizabeth A. Bolden
(74) *Attorney, Agent, or Firm*—Carmody & Torrance LLP (57) ABSTRACT

This invention provides an antimicrobial glass which exhibits excellent dispersing ability into a resin and excellent transparency besides generating small yellowing and a method for manufacturing the antimicrobial glass. In the antimicrobial glass capable of releasing an Ag ion, a shape of the antimicrobial glass is formed into a polyhedron and, at the same time, an average particle size of the antimicrobial glass is set to a value within a range of 0.1 to 300 $\mu$m.

20 Claims, 2 Drawing Sheets

ANTIBACTERIAL GLASS AND METHOD FOR PRODUCTION THEREOF

TECHNICAL FIELD

The present invention relates to an antimicrobial (antibacterial) glass capable of releasing an Ag ion and a manufacturing method thereof, and more particularly to an antimicrobial glass which is excellent in dispersibility into a resin or in transparency and a manufacturing method thereof.

BACKGROUND OF THE INVENTION

Recently, in the field of construction material, home electric appliances (including television sets, personal computers, portable telephones, video cameras and the like), sundries, packaging material and the like, to give an antimicrobial effect, an antimicrobial resin composition which is produced by mixing a given amount of antimicrobial glass into a resin has been used.

As such antimicrobial glass, a glass water treatment agent which is capable of resolving Ag ion therein is disclosed in JP62(1987)-210098A.

This glass water treatment agent is formed of boron silicate based antimicrobial glass which contains 0.2–1.5 parts by weight of mono valent Ag ion based on silver oxide conversion per 100 parts by weight of glass and also contains 20–70 mol % of $B_2O_3$ as a glass component. To be more specific, in examples 2 and 3 of this patent publication, the antimicrobial glass containing 20–30 mol % of $B_2O_3$, 40 mol % of ZnO, 30–40 mol % of $P_2O_5$ and 1 weight % of $Ag_2O$ is disclosed.

Further, in JP01(1989)-313531A, as the antimicrobial resin composition, a synthetic resin molded body containing antimicrobial glass into a resin is disclosed. To explain this synthetic resin molded body specifically, the synthetic resin molded body includes anti microbial glass containing 0.1–20 parts by weight of $Ag_2O$ as mono valent Ag in 100 parts by weight of glass solid formed of one, two or more kinds of network-forming oxides selected from a group consisting of $SiO_2$, $B_2O_3$, $P_2O_5$ and one, two or more kinds of network-modifying oxides selected from a group consisting of $Na_2O$, $K_2O$, CaO, ZnO into a resin. To be more specific, in the embodiment of the above-mentioned patent publication, there is disclosed antimicrobial glass which adds 2 parts by weight of $Ag_{2O}$ to 100 parts by weight of mixture formed of 40 mol % of $SiO_2$, 50 mol % of $B_2O_3$ and 10 mol % of $Na_2O$.

However, the antimicrobial glass disclosed in JP62 (1987)-210098A contains 20–70 mol % of $B_2O_3$ as glass composition. Further, although it is considered that the shape is not taken into account, the antimicrobial glass is whitened or reflocculated so that there has been a problem that the antimicrobial glass exhibits poor transparency and is liable to generate yellowing. Further, there has been also a problem that when the antimicrobial glass is mixed into a resin, the dispersibility of the antimicrobial glass is insufficient.

Accordingly, when the antimicrobial glass which exhibits the poor transparency and the poor dispersibility is mixed into a resin or laminated to a surface of a resin molded product, there has been a problem that color and transparency that the resin per se has are damaged or the resin molded product exhibits poor surface smoothness.

Further, the antimicrobial glass disclosed in JP01(1989)-313531A contains $B_2O_3$ as a main component. Further, in this antimicrobial glass, compounding amounts of network-forming oxide and network-modifying oxide are not optimized. Still further, there has been a problem that since the shape is not taken into consideration, the antimicrobial glass exhibits poor transparency and poor dispersibility or generates yellowing. Still further, there has been a problem that such antimicrobial glass requires an excessively long manufacturing time due to glass composition thereof.

Accordingly, the applicant has already proposed in JP2000-191339A, a dissoluble glass with little yellowing which substantially does not contain $B_2O_3$ but contains $Ag_2O$, ZnO and $P_2O_5$ instead, wherein assuming a total amount to 100 weight %, a content of $Ag_2O$ is set to a value within a range of 0.2 to 5 weight %, a content of ZnO is set to a value within a range of 1 to 50 weight %, and a content of $P_2O_5$ is set to a value within a range of 30 to 80 weight %.

Although the disclosed dissoluble glass has an advantageous effect that yellowing thereof is small, the compounding amounts of ZnO and network-forming oxide (CaO) are not optimized. Accordingly, when a relatively large amount of ZnO is added and the ZnO amount is fluctuated, there has been a problem that the anti microbial glass exhibits poor transparency and poor dispersibility.

Accordingly, as a result of extensive studies, the inventors have found that by limiting the shape and average particle size of the antimicrobial glass respectively, even when the antimicrobial glass contains no ZnO, or the antimicrobial glass contains a relatively large amount of ZnO, or the antimicrobial glass contains a given amount of $B_2O_3$, the antimicrobial glass exhibits small yellowing and it is possible to enhance transparency and dispersibility of the antimicrobial glass.

That is, the inventors have found that irrespective of the glass composition, it is possible to obtain the antimicrobial glass which can be easily manufactured while exhibiting small yellowing and excellent transparency and dispersibility and have completed the present invention.

DISCLOSURE OF INVENTION

According to the present invention, there is provided an antimicrobial glass capable of releasing an Ag ion which is characterized in that the antimicrobial glass has the shape of a polyhedron and also has an average particle size set to a value in the range of 0.1 to 300 μm and the antimicrobial glass can solve the above-mentioned problems.

That is, since the antimicrobial glass has the shape of a polyhedron, an amount of progressing light which is impeded by the antimicrobial glass is small. Further, since the antimicrobial glass is hardly reflocculated (coagulated), it is possible to enhance the transparency of the antimicrobial glass per se.

Further, since the antimicrobial glass has the shape of a polyhedron, when the antimicrobial glass is mixed and dispersed into a resin, the antimicrobial glass can be easily oriented in one fixed direction so that the antimicrobial glass is present uniformly into a resin and it is possible to effectively prevent light scattering derived from the antimicrobial glass into a resin.

Further, since the shape of the antimicrobial glass is a polyhedron and an average particle size is restricted to a given range, the dispersing ability of the antimicrobial glass into a resin may be enhanced.

Further, an another mode of the present invention is directed to a method for producing anti-microbial glass which is characterized by comprising following steps (A) to (C).

(A) a step in which glass material containing at least Ag$_2$O is melted to form a glass melt.
(B) a first grinding step in which the glass melt is ground into rough-ground glass having an average particle size exceeding 300 μm.
(C) a second grinding step in which the glass material is ground into coarsely ground glass having an average particle size in a range of 0.1 to 300 μm and having the shape of a polyhedron.

By producing the antimicrobial glass in this manner, it is possible to effectively obtain the antimicrobial glass which exhibits excellent transparency and dispersibility.

BEST MODE FOR CARRYING OUT THE INVENTION

[First Embodiment]

The first embodiment is directed to antimicrobial glass having the shape of a polyhedron and having an average particle size of 0.5 to 300 μm.

Hereinafter, the shape, the average particle size, the composition of glass and the like of the antimicrobial glass of the first embodiment are specifically explained.

1. Shape

The shape of the antimicrobial glass is polyhedron, that is, is constituted of a plurality of angles and faces. For example, the antimicrobial glass is formed of a polyhedron glass which is made of hexahedron to icosahedron.

Figure 1:
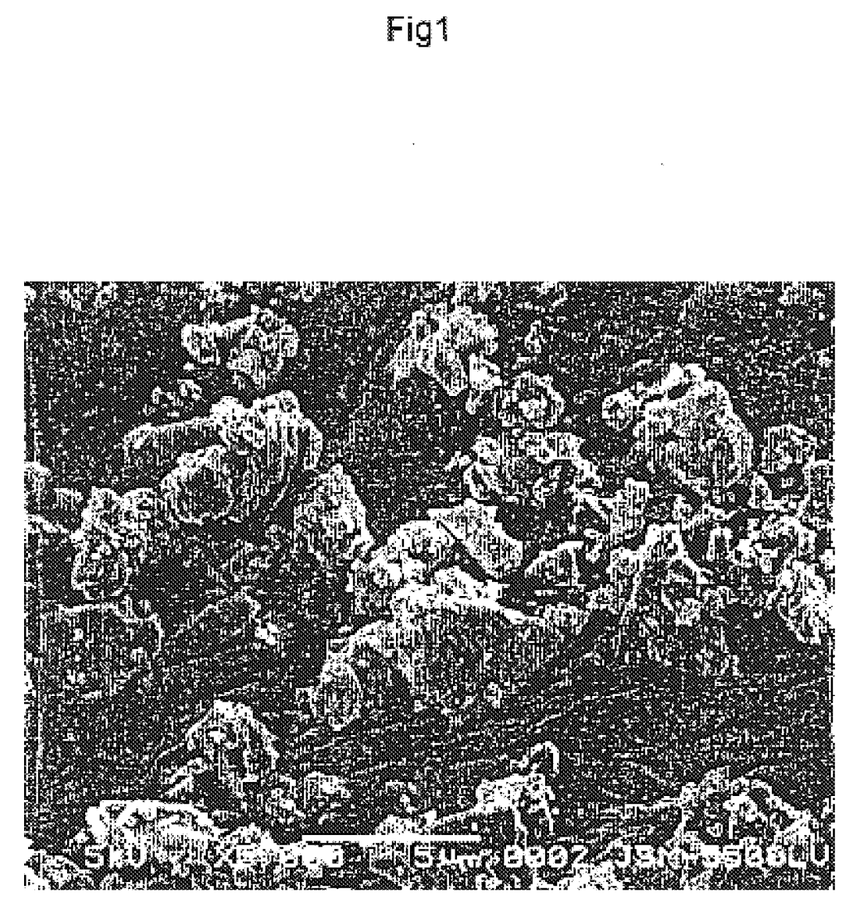
FIG. 1 is a photo-view showing a shape of antimicrobial glass.
Figure 2:
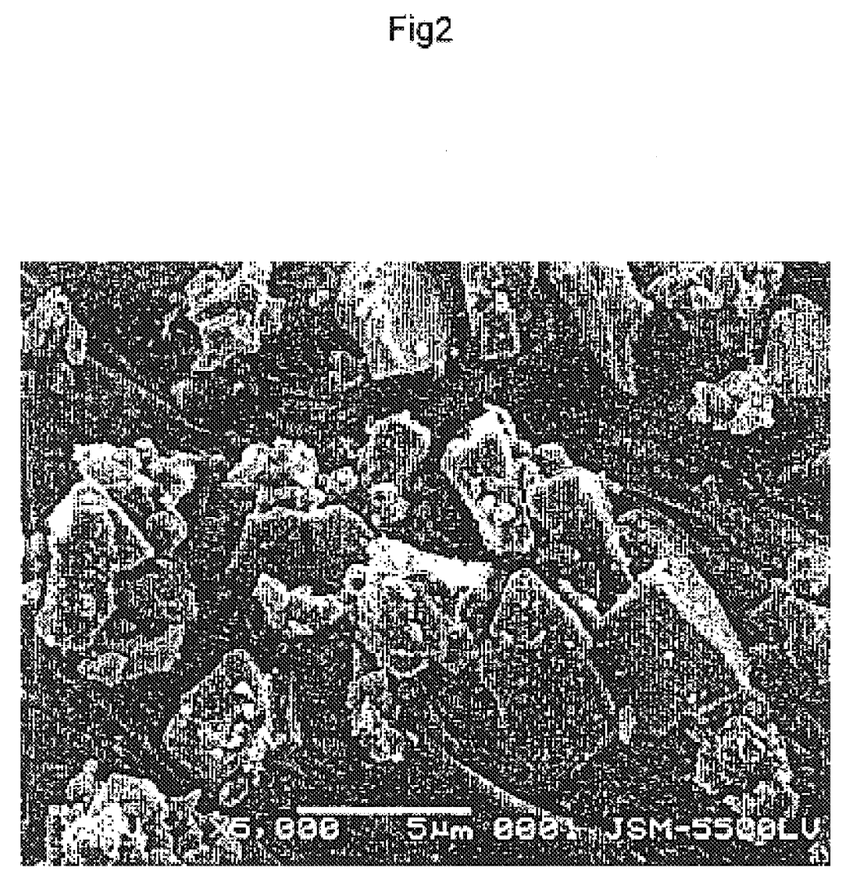
FIG. 2 is a photo-view showing the shape of the antimicrobial glass containing externally deposited particles.

In FIG. 1 and FIG. 2, the shapes of the antimicrobial glass observed using an electron microscope are shown.

FIG. 1 shows the antimicrobial glass which is produced by steps similar to steps of an example 1. FIG. 1 shows that ground fine pieces of the antimicrobial glass are re-flocculated and adhered to the surface of the antimicrobial glass having the shape of a polyhedron. Further, FIG. 2 shows the antimicrobial glass containing externally deposited particles, which is produced by steps similar to steps of an example 3. The drawing shows that although ground fine pieces of the antimicrobial glass are slightly produced, these fine pieces are hardly reflocculated and are independently present without adhering to the surface of the antimicrobial glass having the shape of a polyhedron.

Further, as can be easily understood from these FIG. 1 and FIG. 2, by forming the shape of the antimicrobial glass into polyhedron, different from antimicrobial glass having a spherical shape, light can easily progress or advance in a fixed direction in plane. Accordingly, light scattering derived from the antimicrobial glass can be effectively prevented whereby it is possible to enhance the transparency of the antimicrobial glass.

Further, by forming the antimicrobial glass into polyhedron, not only mixing and dispersing of the antimicrobial glass into a resin are facilitated but also the orientation of the antimicrobial glass in a fixed direction is facilitated when an injection molding is performed. Accordingly, the uniform dispersion of the antimicrobial glass into a resin is facilitated and, at the same time, light scattering due to the antimicrobial glass into a resin can be effectively prevented.

Still further, when the antimicrobial glass has the shape of a polyhedron in this manner, the antimicrobial glass is hardly reflocculated at the time of production or use thereof and hence, control of an average particle size of the antimicrobial glass at the time of producing the antimicrobial glass and handling of the antimicrobial glass at the time of using the antimicrobial glass in the producing steps can be facilitated.

Further, with respect to the shape of the antimicrobial glass, it is preferable that a periphery of the polyhedron is covered with inorganic particles and organic particles or either one of these particles.

Due to such a constitution, the control of releasing speed of an Ag ion is facilitated and dispersibility of the antimicrobial glass can be further enhanced.

Still further, as the particles which cover the antimicrobial glass, it is preferable to use one or combination of titanium oxide, silicon oxide, colloidal silica, zinc oxide, tin oxide, lead oxide, white carbon, acrylic particles, styrene particles, polycarbonate particles and the like.

Further, although the method for covering the antimicrobial glass with the particles is not specifically limited, for example, it is preferable that the antimicrobial glass and the particles are uniformly mixed and, thereafter, are heated at a temperature of 600 to 1200 degree centigrade to be fused to the glass or are fixed to the antimicrobial glass using a bonding agent.

Here, since the antimicrobial glass of the present invention has a shape of polyhedron, the movement of the particles which cover the antimicrobial glass is confined by faces of the polyhedron thus also giving rise to an advantageous effect that the particles can uniformly cover the periphery of the antimicrobial glass.

2. Average Particle Size

Further, the average particle size of the antimicrobial glass is set to a value which falls within a range of 0.1 to 300 μm. The reason is that when the average particle size is set to a value of 0.1 μm, mixing and dispersing of the anti microbial glass into a resin become easy or light scattering is liable to occur easily so that the transparency is degraded. Further, when the average particle size falls in such a range, even when the antimicrobial glass is added to a molded product containing the antimicrobial glass, the molded product exhibits the excellent surface smoothness. On the other hand, when the average particle size exceeds 300 μm, mixing and dispersing of the antimicrobial glass into a resin or handling of the antimicrobial glass become difficult or when the antimicrobial glass is added to a molded product, this may give rise to deterioration of the surface smoothness. Accordingly, it is preferable to set the average particle size of the antimicrobial glass to a value within a range from 0.5 to 50 μm and, it is more preferable to set the average particle size of the antimicrobial glass to a value within a range from 1 to 20 μm.

Here, the average particle size of the anti microbial glass can be easily measured using a laser type particle counter, a settling type particle size distribution meter or based on an electron microscope photograph of the antimicrobial glass.

3. Composition of Glass

As the glass composition of the antimicrobial glass, it is preferable that the antimicrobial glass includes Ag$_2$O, ZnO, CaO, B$_2$O$_3$ and P$_2$O$_5$. When the total amount is set to 100 weight %, it is preferable to set a content of Ag$_2$O to a value within a range of 0.2 to 5 weight %, to set a content of ZnO to a value within a range of 1 to 50 weight %, to set a content of CaO to a value within a range of 0.1 to 15 weight %, to set a content of B$_2$O$_3$ to a value within a range of 0.1 to 15 weight %, and to set a content of P$_2$O$_5$ to a value within a range of 30 to 80 weight % and, at the same time, to set a weight ratio of ZnO/CaO to a value within a range of 1.1 to 15.

(1) $Ag_2O$ $Ag_2O$ is an indispensable constituent component in the antimicrobial glass of the present invention. The antimicrobial glass which exhibits excellent antimicrobial property for a long period can be produced by melting a glass component so as to release an Ag ion.

Here, it is preferable to set a content of the $Ag_2O$ to a value within a range of 0.2 to 5 weight %. The reason is as follows. That is, when the content of the $Ag_2O$ assumes a value which is below 0.2 weight %, the antimicrobial property of the antimicrobial glass becomes insufficient, while to obtain a given antimicrobial effect, a large amount of antimicrobial glass becomes necessary. On the other hand, when the content of the $Ag_2O$ exceeds 5 weight %, the antimicrobial glass is more liable to be discolored or it pushes up the cost and hence, it is disadvantageous economically. Accordingly, from a viewpoint that the favorable balance among the antimicrobial property of the antimicrobial glass, the prevention of discoloration and the like can be obtained, it is preferable to set the content of $Ag_2O$ to a value within a range of 1 to 4 weight %. It is more preferable to set the content of $Ag_2O$ to a value within a range of 1.5 to 3 weight %.

(2) ZnO

ZnO performs a function of a network-modifying oxide in the antimicrobial glass, a function of preventing yellowing and a function of enhancing antimicrobial property.

Here, it is preferable to set a content of ZnO within a range of 2 to 60 weight % with respect to a total amount. The reason is as follows. That is, when the content of ZnO assumes a value below 2 weight %, there may be case that the yellowing preventing effect and the antimicrobial property enhancing effect cannot be expected. On the other hand, when the content of ZnO exceeds 60 weight %, there may be a case that the transparency of the antimicrobial glass is deteriorated and the mechanical strength becomes insufficient. Accordingly, from a viewpoint of taking the more favorable balance among the prevention of discoloration, transparency and the like of the antimicrobial glass, it is preferable to set the content of ZnO to a value within a range of 5 to 50 weight % with respect to the total amount and it is more preferable to set the content of ZnO to a value within a range of 10 to 40 weight % with respect to the total amount.

Further, it is preferable to set the content of ZnO in view of a content of CaO which will be explained later. To be more specific, it is preferable to set the weight ratio expressed by ZnO/CaO to a value within a range of 1.1 to 1.5. The reason is that when the weight ratio assumes a value below 1.1, there may be a case that it is difficult to efficiently prevent yellowing of the antimicrobial glass, while, to the contrary, when the weight ratio exceeds 15, there may be a case that the antimicrobial glass suffers from whitening or, in a reverse manner, yellowing. Accordingly, it is more preferable to set the weight ratio expressed by ZnO/CaO to a value within a range of 1.2 to 10 and it is still more preferable to set the weight ratio expressed by ZnO/CaO to a value within a range of 1.5 to 8.

(3) CaO

With the use of CaO in the antimicrobial glass of the present invention, CaO basically performs the function of the network-modifying oxide and, at the same time, lowers a heating temperature at the time of forming the antimicrobial glass. Further, CaO performs the function of preventing yellowing along with ZnO.

Here, it is preferable to set a content of CaO to a value within a range of 0.1 to 15 weight % with respect to the total amount of the microbial glass. The reason is that when the content of CaO becomes less than 0.1 weight %, there is a possibility that addition effects (yellowing preventing function and melting temperature lowering effect) cannot be exhibited, while when the content of CaO exceeds 15 weight %, the transparency of the antimicrobial glass is lowered to the contrary. Accordingly, from a viewpoint of taking a favorable balance between the melting temperature lowering effect and transparency and the like of the antimicrobial glass, it is preferable to set the content of CaO to a value within a range of 1 to 10 weight %. Further, it is the most preferable to set the content of CaO to a value within a range of 2 to 7 weight %.

(4) $B_2O_3$ $B_2O_3$ is an indispensable constituent component in the antimicrobial glass of the present invention. Although $B_2O_3$ basically performs the function of the network-forming oxide, $B_2O_3$ also relates to the transparency improving function of the antimicrobial glass and the uniform releasing property of an Ag ion in the present invention.

Here, it is preferable to set a content of $B_2O_3$ to a value within a range of 0.1 to 15 weight %. The reason is that when the content of $B_2O_3$ becomes less than 0.1 weight %, there is a possibility that the transparency of the antimicrobial glass is lowered or the uniform releasing property of the Ag ion and mechanical strength are reduced, while when the content of $B_2O_3$ exceeds 15 weight %, there is a possibility that the antimicrobial glass is easily subjected to yellowing or lacks in hardness so that mechanical strength is reduced. Accordingly, from a viewpoint of taking a favorable balance between the transparency of the antimicrobial glass and the discoloration preventing property and the like, it is more preferable to set the content of $B_2O_3$ to a value within a range of 1 to 12 weight %. Further, it is the most preferable to set the content of $B_2O_3$ to a value within a range of 5 to 10 weight %.

(5) $P_2O_5$ $P_2O_5$ is an indispensable constituent component in the antimicrobial glass of the present invention. Although $P_2O_5$ basically performs the function of the network-forming oxide, $P_2O_5$ also relates to the transparency improving function of the antimicrobial glass and the uniform releasing property of an Ag ion in the present invention.

Here, it is preferable to set a content of $P_2O_5$ to a value within a range of 30 to 80 weight %. The reason is that when the content of $P_2O_5$ becomes less than 30 weight %, there is a possibility that the transparency of the antimicrobial glass is lowered or the uniform releasing property of the Ag ion and mechanical strength are reduced, while when the content of $P_2O_5$ exceeds 80 weight %, there is a possibility that the antimicrobial glass is easily subjected to yellowing or lacks in hardness so that mechanical strength is reduced. Accordingly, from a viewpoint of taking a favorable balance between the transparency of the antimicrobial glass and the discoloration preventing property and the like, it is more preferable to set the content of $P_2O_5$ to a value within a range of 30 to 75 weight %. Further, it is the most preferable to set the content of $P_2O_5$ to a value within a range of 30 to 70 weight %.

(6) Other Components i) $CeO_2$ $CeO_2$ is an arbitrary constituent component in the antimicrobial glass of the present invention and basically performs the function of network-modifying oxide. However, when $CeO_2$ is used in the present invention, $CeO_2$ also exhibits the function of improving transparency of the antimicrobial glass. Further, with the addition of $CeO_2$, it is also possible to enhance the discoloration prevention property against electron beams.

Here, it is preferable to set a content of $CeO_2$ to a value within a range of 0.1 to 5 weight % with respect to a total amount. The reason is that when the content of $CeO_2$ is less than 0.1 weight %, there is a possibility that an addition effect (transparency improving function) cannot be exhibited, while when the content of $Ceo_2$ exceeds 5 weight %, this pushes up the cost and it is disadvantageous economically. Accordingly, from a viewpoint of taking a favorable balance between economy and discoloration preventing property or the like of the antimicrobial glass, it is more preferable to set the content of $CeO_2$ to a value within a range of 0.2 to 3 weight %. It is further preferable to set the content of $CeO_2$ to a value within a range of 0.3 to 2 weight %.

ii) MgO

MgO is an arbitrary constituent component in the antimicrobial glass of the present invention and basically performs the function of network-modifying oxide. However, when MgO is used in the present invention, MgO also exhibits the function of improving transparency of the antimicrobial glass.

Here, it is preferable to set a content of MgO to a value within a range of 0.1 to 15 weight % with respect to a total amount. The reason is that when the content of MgO is less than 0.1 weight %, there is a possibility that an addition effect (transparency improving function) cannot be exhibited, while when the content of MgO exceeds 15 weight %, this pushes up the cost and it is disadvantageous economically. Accordingly, from a viewpoint of taking a favorable balance between economy and discoloration preventing property or the like of the antimicrobial glass, it is more preferable to set the content of MgO to a value within a range of 0.5 to 12 weight %. It is the most preferable to set the content of MgO to a value within a range of 1 to 10 weight %.

iii) $Na_2O$ $Na_2O$ is an arbitrary constituent component in the antimicrobial glass of the present invention and basically performs the function of network-modifying oxide when $Na_2O$ is used in the present invention. However, $Na_2O$ also exhibits the function of improving transparency of the antimicrobial glass.

Here, it is preferable to set a content of $Na_2O$ to a value within a range of 0.1 to 10 weight % with respect to a total amount. The reason is that when the content of $Na_2O$ is less than 0.1 weight %, there is a possibility that an addition effect (transparency improving function) cannot be exhibited, while when the content of $Na_2O$ exceeds 10 weight %, there is a possibility that this lowers transparency of the antimicrobial glass. Accordingly, from a viewpoint of taking a favorable balance between transparency and discoloration preventing property or the like of the antimicrobial glass, it is more preferable to set the content of $Na_2O$ to a value within a range of 0.2 to 5 weight % with respect to the total amount. It is further preferable to set the content of $Na_2O$ to a value within a range of 0.5 to 3 weight %.

iv) $Al_2O_3$ $Al_2O_3$ is an arbitrary constituent component in the antimicrobial glass of the present invention and basically performs the function of network-forming oxide when $Al_2O_3$ is used in the present invention. However, in the present invention, besides the above-mentioned function, $Al_2O_3$ can also exhibit the function of improving mechanical strength and transparency of the antimicrobial glass.

Here, it is preferable to set a content of $Al_2O_3$ to a value within a range of 0.1 to 20 weight % with respect to a total amount. The reason is that when the content of $Al_2O_3$ is less than 0.1 weight %, there is a possibility that an addition effect (transparency improving function) cannot be exhibited, while when the content of $Al_2O_3$ exceeds 20 weight %, there is a possibility that this lowers transparency of the antimicrobial glass. Accordingly, from a viewpoint of taking a favorable balance between mechanical strength and the transparency of the antimicrobial glass, it is more preferable to set the content of $Al_2O_3$ to a value within a range of 1 to 15 weight % with respect to the total amount. It is further preferable to set the content of $Al_2O_3$ to a value within a range of 2 to 10 weight %.

v) Other Constituent Components

It is also preferable to add given quantities of $K_2O$, $SiO_2$, BaO and the like within a scope of the object of the present invention as network-modifying components.

[Second Embodiment]

The second embodiment is directed to an antimicrobial glass having a shape of polyhedron having an average particle size of 0.5 to 300 $\mu$m. As the glass composition, although the antimicrobial glass does not substantially contain ZnO, the antimicrobial glass contains $Ag_2O$, CaO, $B_2O_3$ and $P_2O_5$ in place of ZnO. Further, assuming a total amount as 100 weight %, a content of $Ag_2O$ is set to a value within a range of 0.2 to 5 weight %, a content of CaO is set to a value within a range of 15 to 50 weight %, a content of $B_2O_3$ is set to a value within a range of 0.1 to 15 weight % and a content of $P_2O_5$ is set to a value within a range of 30 to 80 weight %. Further, the weight ratio of $CaO/Ag_2O$ is set to a value within a range of 5 to 15. Hereinafter, the second embodiment is explained while focusing on the glass composition and the like which feature the antimicrobial glass of the second embodiment.

1. Shape and Average Particle Size

The shape and the average particle size of the antimicrobial glass according to the second embodiment can have the same content as the first embodiment.

Accordingly, it is preferable to form the antimicrobial glass according to the second embodiment into hexahedron to decahedron and it is also preferable to set the average particle size to a value within a range of 0.1 to 300 $\mu$m.

2. Glass Composition (1) $Ag_2O$

With respect to $Ag_2O$, $Ag_2O$ can have the same content as that of the first embodiment, accordingly, it is preferable to set a content of $Ag_2O$ to a value within a range of 0.2 to 5 weight (2) CaO With the use of CaO in the antimicrobial glass of the present invention, CaO basically performs the function of network-modifying oxide and, at the same time, performs the function of lowering heating temperature and the function of preventing yellowing at the time of producing the antimicrobial glass.

Here, it is preferable to set a content of CaO to a value within a range of 15 to 50 weight % with respect to a total amount. The reason is that when the content of CaO is less than 15 weight %, since the antimicrobial glass substantially does not contain ZnO, there is a possibility that the yellowing preventing function and the melting temperature lowering effect can not be exhibited, while when the content of CaO exceeds 50 weight %, the transparency of the antimicrobial glass is lowered to the contrary.

Accordingly, from a viewpoint of obtaining a favorable balance between the melting temperature lowering effect and transparency or the like of the antimicrobial glass, it is preferable to set the content of CaO to a value within a range of 20 to 40 weight %. Further, it is the most preferable to set the content of CaO to a value within a range of 25 to 35 weight %.

Further, in view of the fact that the above-mentioned $Ag_2O$ becomes a cause of yellowing, it is preferable to set the content of CaO which exhibits the yellowing preventing function in view of the content of $Ag_2O$. To be more specific, it is preferable to set the weight ratio expressed by $CaO/Ag_2O$ to a value within a range of 5 to 15. The reason is that when the weight ratio is below 5, there is a possibility that the yellowing of the antimicrobial glass can not be efficiently prevented, while when the weight ratio exceeds 15, the antimicrobial glass suffers from whitening or suffers from yellowing to the contrary. Accordingly, it is preferable to set the weight ratio expressed by $CaO/Ag_2O$ to a value within a range of 6 to 12. It is more preferable to set the weight ratio within a range of 7 to 10.

(3) $B_2O_3$

With respect to $B_2O_3$, the second embodiment can have the same content as that of the first embodiment. Accordingly, it is preferable to set a content of $B_2O_3$ to a value within a range of 0.1 to 15 weight % with respect to a total amount.

(4) $P_2O_5$

With respect to $P_2O_5$, the second embodiment can have the same content as that of the first embodiment. Accordingly, it is preferable to set a content of $P_2O_5$ to a value within a range of 30 to 80 weight % with respect to a total amount.

(5) Other Components

Also with respect to $CeO_2$, MgO, $Na_2O$, $Al_2O_3$, $K_2O$, $SiO_2$, BaO and the like, the second embodiment can have the same content as those of the first embodiment.

Although the antimicrobial glass of the second embodiment is characterized by substantially containing no ZnO in the glass composition, to be more specific, it is preferable to set the content of ZnO to a value equal to or less than 1 weight %. It is more preferable to set the content of ZnO to a value equal to or less than 0.5 weight %. It is further preferable to set the content of ZnO to a value equal to or less than 0.1 weight

[Third Embodiment]

The third embodiment is directed to an antimicrobial glass which includes an antimicrobial glass having the shape of a polyhedron (hereinafter also referred to as a polyhedron glass) having the average particle size of 0.5 to 300 $\mu$m and externally deposited particles having the average particle size which is a value within range of 0.01 to 100 $\mu$m which is smaller than the average particle size of the polyhedron glass.

Here, even when the polyhedron glass and the externally deposited particles are not melted to each other, it is confirmed that the antimicrobial glass can sufficiently exhibits the reflocculating preventing effect of the polyhedron glass and an effect of controlling Ag ion releasing speed.

Hereinafter, the externally deposited particles and the addition amount of the externally deposited particles which feature the third embodiment are explained specifically.

(1) Kinds

As the externally deposited particles, it is preferable to use particles which are of the same kind as particles which are used for covering the polyhedron glass. Accordingly, it is preferable to use a single kind or a combination of more than two kinds selected from a group consisting of titanium oxide, silicon oxide, colloidal silica, zinc oxide, tin oxide, lead oxide, white carbon, acrylic particles, styrene particles, polycarbonate particles and the like. Further, although the externally deposited particles may be added after producing the polyhedron glass, it is preferable to add the externally deposited particles during the production of the polyhedron glass. By adding the externally deposited particles during the production of the polyhedron glass, it is possible to prevent the production of excessively small polyhedron glass so that the average particle size can be easily controlled such that the averaga particle size falls within a given range.

Here, in adding the externally deposited particles during the production of polyhedron glass, it is preferable to use the externally deposited particles which are uniformly dispersed in a dispersing agent for polyhedron glass such as isopropanol, toluene or the like without being dissolved in the dispersing agent. Accordingly, it is preferable to use colloidal silica and white carbon as the externally deposited particles.

(2) Average Particle Size

The reason that the average particle size of the externally deposited particles is limited to the value within a range of 0.01 to 100 $\mu$m is as follows. That is, when the average particle size of the externally deposited particles assumes a value less than 0.01 $\mu$m the reflocculation preventing effect of the polyhedron glass is deteriorated or it is necessary to excessively increase an addition amount of the externally deposited particles to obtain a given reflocculation preventing effect. On the other hand, when the average particle size of the externally deposited particles exceeds 100 $\mu$m, there exists a possibility that the transparency is lowered or the control of Ag ion releasing speed becomes difficult.

Accordingly, it is more preferable to set the average particle size of the externally deposited particles to a value within a range of 0.03 to 50 $\mu$m. It is further preferable to set the average particle size of the externally deposited particles to a value within a range of 0.05 to 10 $\mu$m.

(3) Addition Amount

It is preferable to set the addition amount of the externally deposited particles to a value within a range of 0.1 to 30 parts by weight with respect to 100 parts by weight of the polyhedron glass.

The reason is as follows. That is, when the addition amount of the externally deposited particles assumes a value less than 0.1 parts by weight, there arises a case that it is impossible to obtain the sufficient reflocculation preventing effect of the polyhedron glass and the sufficient effect to control the Ag ion releasing speed. On the other hand, when the addition amount of the externally deposited particles exceeds 30 parts by weight, there arises a case that the transparency is degraded and the mixing and dispersing ability of the polyhedron glass into a resin is deteriorated.

Accordingly, it is preferable to set the addition amount of the externally deposited particles to a value within a range of 0.5 to 20 parts by weight with respect to 100 parts by weight of the polyhedron glass. It is further preferable to set the addition amount of the externally deposited particles to a value within a range of 1 to 10 parts by weight.

(4) Adding Method

A method for adding the externally deposited particles is not particularly limited. The method may be a method which adds the externally deposited particles during the production of the polyhedron glass, a method which adds the externally deposited particles after the production of the polyhedron glass, or a method which adds the externally deposited particles simultaneously with mixing and dispersing of the polyhedron glass into a resin.

Further, when the externally deposited particles is added during the production of the polyhedron glass, it is preferable to add the externally deposited particles at a time that the polyhedron glass is finely ground. The reason is that although it is known that the excessively small polyhedron glass is produced at the time of fine grinding and these finely ground polyhedrons are reflocculated with the relatively large polyhedron glass, it is possible to selectively prevent such reflocculation by the addition of the externally deposited particles.

[Fourth Embodiment]

The fourth embodiment is directed to an antimicrobial glass which makes a surface of a polyhedron glass having an average particle size of 0.5 to 300 μm subjected to surface treatment which is performed using a coupling agent Hereinafter, the coupling agent and a treatment amount thereof and the like which feature the fourth embodiment are specifically explained.

(1) Coupling Agent

As the coupling agent, although a silane coupling agent, an aluminum coupling agent, a titanium coupling agent and the like can be used, it is preferable to use the silane coupling agent because the silane coupling agent exhibits an excellent adhesive force thereof to the polyhedron glass.

Further, as kinds of preferred silane coupling agents, γ-aminopropyltrimethoxysilane, γ-aminopropyltriethoxysilane, γ-glycidoxypropyltrimethoxysilane, γ-glycidoxypropyl-trietho xysilane, γ-mercaptopropyltrimethoxysilane, γ-mercaptopropyl-triethoxysilane, or one single kind or two or more kinds of silane coupling agents having a following structural formula are named.

$RO(CH_2CHO)_nCH_2CH_2CSi(OR')_3$ (R being a methyl radical, an ethyl radical or hydrogen and R' being a methyl radical or an ethyl radical, and n being an integer from 1 to 10)

(2) Addition Amount

It is preferable to set the treatment amount of the coupling agent to a value within a range of 0.01 to 30 parts by weight with respect to 100 parts by weight of the polyhedron glass. The reason is as follows. That is, when the treatment amount of the coupling agent assumes a value less than 0.01 parts by weight, there arises a case that it is impossible to obtain the sufficient reflocculation preventing effect of the polyhedron glass and the sufficient effect to control the Ag ion releasing speed or the mixing and dispersing of the coupling agent into a resin is lowered.

On the other hand, when the treatment amount of the coupling agent exceeds 30 parts by weight, there arises a case that the transparency of the polyhedron glass is degraded and the mixing and dispersing ability of the antimicrobial glass (polyhedron glass) into a resin is deteriorated to the contrary.

Accordingly, it is preferable to set the treatment amount of the coupling agent to a value within a range of 0.1 to 20 parts by weight with respect to 100 parts by weight of the polyhedron glass. It is further preferable to set the treatment amount of the coupling agent to a value within a range of 0.5 to 10 parts by weight.

(3) Adding Method

Further, a method for treating the coupling agent is not particularly limited. In the same manner as the externally deposited particles, the method may be a method which treats the coupling agent during the production of the polyhedron glass, a method which treats the coupling agent after the production of the polyhedron glass, or a method which treats the coupling agent simultaneously with mixing and dispersing of the polyhedron glass into a resin.

Further, when the coupling agent is added during the production of the polyhedron glass, it is preferable to add the coupling agent at a time that the polyhedron glass is finely ground in the same manner as the externally deposited particles.

Still further, to bring the coupling agent and the polyhedron glass into uniform contact with each other, it is preferable to dilute the coupling agent in advance using a solvent.

[Fifth Embodiment]

The fifth embodiment is directed to a method for producing the antimicrobial glasses of the first to fourth embodiments and is characterized by including at least the steps A to C as mentioned previously.

Hereinafter, the steps A to C for producing the antimicrobial glass of the present invention are specifically explained.

(1) Step for Mixing Glass Raw Materials

This step is a step in which glass raw materials containing $Ag_2O$, $ZnO$, $CaO$, $B_2O_3$ and $P_2O_5$ and the like (first embodiment) or glass raw materials containing $Ag_2O$, $CaO$, $B_2O_3$ and $P_2O_5$ and the like while substantially containing no $ZnO$ (second embodiment) are accurately weighed and are uniformly mixed. Here, in mixing these glass raw materials, it is preferable to use a mixing apparatus (mixer) such as a universal agitator (planetary mixer), an alumina porcelain grinder, a ball mill, a propeller mixer or the like. For example, when the universal agitator is used, it is preferable to agitate and mix the glass raw materials under conditions that the number of revolution is set to 100 rpm, the number of rotation is set to 250 rpm and the universal agitator is operated for 30 minutes to 5 hours.

(2) Step for Melting Glass Raw Material (Step A)

This step is a step in which glass melt is produced by melting the uniformly mixed glass raw material using a glass melting furnace as an example.

Further, as melting conditions, it is preferable to set a melting temperature to 600 to 1500 degree centigrade and to set a melting time to a value within 0.1 to 24 hours. This is because that by satisfying such melting conditions, the productivity of the glass melt can be enhanced and yellowing of the anti microbial glass at the time of production can be reduced as small as possible.

(3) Grinding Step of Antimicrobial Glass (Step B and Step C)

This step is a step in which the obtained molten glass is ground so as to produce the antimicrobial glass of the present invention being a polyhedron and having a given average particle size.

To be more specific, it is preferable to perform following coarse grinding (including water grinding), intermediate grinding and fine grinding. To perform grinding in this manner, it is possible to efficiently obtain the antimicrobial glass having a uniform average particle size. However, to control the average particle size more finely depending on applications, it is also preferable to perform the sieve treatment by providing a classifying step after the grinding step.

i) Coarse Grinding (step B)

The coarse grinding is a step in which the antimicrobial glass is ground until the average particle size becomes approximately 10 mm. As such coarse grinding, it is preferable to use water granulating in which the glass melt is filled into calm water to make the antimicrobial glass have a given average particle size.

Here, it is confirmed by an electron microscope that the antimicrobial glass obtained by coarse grinding assumes a block-like shape having no corners.

ii) Intermediate Grinding (this Step Partially includes Step C)

The intermediate grinding is a step in which the antimicrobial glass which is already subjected to the coarse grinding is ground such that the average particle size assumes approximately 100 µm.

Usually, it is preferable to perform the intermediate grinding in two stages consisting of a primary intermediate grinding and a second intermediate grinding.

The primary intermediate grinding is a step in which the antimicrobial glass having the average particle size of approximately 10 mm is ground to the antimicrobial glass having the average particle size of approximately 1 mm. It is preferable to perform the grinding using rotary rollers or the like.

The secondary intermediate grinding is a step in which the antimicrobial glass having the average particle size of approximately 1 mm is ground to the antimicrobial glass having the average particle size of approximately 400 µm. It is preferable to perform the grinding using a rotary mill or the like.

It is confirmed by an electron microscope that the antimicrobial glass after the secondary intermediate grinding is formed into a polyhedron having corners.

iii) Fine Grinding (Step C)

The fine grinding is a step in which the antimicrobial glass after intermediate grinding is ground such that the average particle size is set to a value within a range of 0.1 to 300 µm. To perform such fine grinding, for example, a rotary mill, rotary rollers, a vibrating mill, a ball mill, a sand mill or a jet mill can be used. However, it is preferable, in particular, to use a fine grinding mill such as the vibration mill and the jet mill. With the use of such a fine grinding mill, it is possible to impart a proper shearing force to the coarsely ground glass so that the antimicrobial glass which is formed of a polyhedron and has a given average particle size can be effectively obtained without producing the antimicrobial glass having the excessively small particle size.

To compare the vibration ball mill and the jet mill, the use of the vibration ball mill has an advantage that a treatment amount per one operation is large and the structure is simple as the fine grinding device. On the other hand, the use of the jet mill has an advantageous effect that a rate of reflocculation of antimicrobial glass is small and hence, the antimicrobial glass can be agitated in a relatively short time. Further, with the use of the jet mill, for example, it is unnecessary to add externally deposited particles and hence, it is possible to obtain the antimicrobial glass with small reflocculation as shown in FIG. 2. Accordingly, it is preferable to selectively use the fine grinding device depending on the applications of the antimicrobial glass.

Besides the above, it is confirmed based on an electron microscope photograph that the antimicrobial glass which is subjected to the fine grinding with the use of the vibration ball mill or the jet mill is formed of a polyhedron having a large number of corners compared to the antimicrobial glass after the intermediate grinding.

[Sixth Embodiment]

An antimicrobial molded product according to the sixth embodiment is produced by mixing a given amount of at least one of antimicrobial glasses of the first to fourth embodiments into a resin so as to produce the antimicrobial resin product and, thereafter, by molding the antimicrobial resin compound into a given shape using a molding machine.

(1) Resin

In molding an antimicrobial molded product (antimicrobial resin compound), it is possible to mix the antimicrobial glass into following resins.

As preferred resin, one kind or a combination of two or more kinds of a polyethylene resin, a polypropylene resin, a polyethylene terephthalate resin, a polybutylene terephthalate resin, a polycarbonate resin, a styrene-based resin, a vinylidene chloride resin, a vinyl acetate resin, a polyvinyl alcohol resin, a fluoric system resin, a polyarylene resin, an acrylic resin, an epoxy-based resin, a vinyl chloride resin, an ionomer resin, a polyamide-based resin, a polyacetal-based resin, a phenol resin and a melamine resin are used.

Further, in using these kinds of resins, to be more specific, it is preferable to use the resin having light transmissivity which is expressed by a following formula and falls within a range of 50 to 100%. It is more preferable to use the resin having light transmissivity which falls within a range of 80 to 100%. Here, a transmitting light amount or an incident light amount can be measured using an absorption meter or a light amount meter (power meter). In measuring the transmitting light amount or the incident light amount, the transparent resin in a plate shape having a thickness of 1 mm, for example, can be used.

Light transmissivity (%)=transmitting light amount/incident light amount×100

Besides the above, it is also preferable to add pigment, paint, die or the like into these resins.

(2) Addition Amount of Antimicrobial Glass

It is preferable to set the addition amount of the antimicrobial glass to a value within a range of 0.01 to 10 parts by weight with respect to 100 parts by weight of a resin. The reason is as follows. That is, when the addition amount of the antimicrobial glass assumes a value less than 0.01 parts by weight, there arises a case that the antimicrobial property which the antimicrobial glass can exhibit is reduced. On the other hand, when the addition amount of the microbial glass exceeds 10 parts by weight, there arises a case that the mechanical strength of the antimicrobial resin compound is reduced, the uniform mixing of the antimicrobial glass into a resin is difficult, or the transparency of the obtained antimicrobial resin compound is degraded. Accordingly, from a viewpoint of favorable balance between the antimicrobial property and the mechanical strength or the like in the antimicrobial resin compound, it is preferable to set the addition amount of the antimicrobial glass to a value within a range of 0.1 to 5 parts by weight with respect to 100 parts by weight of a resin. It is further preferable to set the addition amount of the antimicrobial glass to a value within a range of 0.3 to 3 parts by weight.

(3) Manner of Mixing Antimicrobial Glass

In mixing the antimicrobial glass into a resin, an agitation mixing method, a kneading method, a coating method, a diffusion method and the like can be adopted. For example, when the agitation mixing method is adopted, it is preferable to perform agitation and mixing for 10 minutes to 24 hours at a room temperature (25 degree centigrade). Further, in mixing the antimicrobial glass, it is preferable to use a mixing device such as an alumina porcelain grinder, a ball mill, a propeller mixer, three rollers, a V blender or the like. It is further preferable to adjust the viscosity of a resin by adding an organic solvent or a lubricant.

(4) Antimicrobial Molded Product

The configuration of the antimicrobial molded product is not limited in particular. That is, the configuration of the antimicrobial molded product may be a configuration obtained by processing the antimicrobial resin compound per se into a given shape or a configuration obtained by laminating the antimicrobial molded product to a surface of a molded product. Further, the configuration of the antimicrobial molded product may be suitably adopted depending on applications. For example, it is sufficient if the antimicrobial resin compound can be laminated to the surface of the molded product such as a bag, shoes, toys, clothes, underwear, stockings, bathtub or the like.

Further, when the antimicrobial molded product is produced by processing the antimicrobial resin compound per se, it is preferable to form the antimicrobial molded product into a plate shape, a film shape, a rectangular parallelepiped shape, a cubic shape, a spherical shape, a rod-like shape or an irregular shape.

EXAMPLES

The present invention is further explained in detail based on examples hereinafter. However, the explanation described hereinafter is made only for an illustration purpose and the present invention is not limited by the description.

Example 1
1. Production of Antimicrobial Glass
i) Melting Step

Assume a total amount of the antimicrobial glass (A composition) as 100 weight %, respective glass raw materials are agitated until these raw materials are uniformly mixed using a universal mixer under conditions that the mixer is operated at a rotational speed of 250 rpm for 30 minutes such that the composition ratio of $P_2O_5$ assumes 50 weight %, the composition ratio of CaO assumes 5 weight %, the composition ratio of $Na_2O$ assumes 1.5 weight %, the composition ratio of $B_2O_3$ assumes 10 weight %, the composition ratio of $Ag_2O$ assumes 3 weight %, the composition ratio of $CeO_2$ assumes 0.5 weight %, the composition ratio of ZnO assumes 30 weight %. Subsequently, using a melting furnace, the glass raw materials are heated under conditions of 1280 degree centigrade for three hours and a half so as to produce a glass melt.

ii) Water Granulating Step

The glass melt taken out from a glass melting furnace is made to flow into calm water having a temperature of 25 degree centigrade so that the glass melt is subjected to water granulating thus producing coarsely ground glass having an average particle size of approximately 10 mm. The coarsely ground glass at this stage is observed using an optical microscope and it is confirmed that the coarsely ground glass has a block-like shape and has no corners and faces.

iii) Intermediate Grinding

Subsequently, using a pair of alumina-made rotary rollers (made of Tokyo Atomizer Inc. Roller Crusher), under conditions that a gap is set to 1 mm and a rotational speed is set to 150 rpm, the coarsely ground glass is supplied to the rollers from a hopper using the deadweight of the coarsely ground glass thus performing primary intermediate grinding (average particle size being 1000 $\mu$m). Further, using an alumina-made rotary grinder (made of Chuo Kakoki Inc. Premax), under conditions that a gap is set to 400 $\mu$m and a rotational speed is set to 700 rpm, the antimicrobial glass which is subjected to the primary intermediate grinding is subjected to the secondary intermediate grinding thus reducing the average particle size to approximately 400 $\mu$m. Here, the coarsely ground glass after the secondary intermediate grinding is observed using an electron microscope and it is confirmed that at least 50 weight % or more of the coarsely ground glass exhibit a polyhedron having corners and faces.

iv) Fine Grinding

Subsequently, in the inside of a vibration ball mill having an inside volume of 105 litters (made of Chuo Kakoki Shoji Inc.), as media, 210 kg of alumina balls having a diameter of 10 mm, 20 kg of the antimicrobial glass which is already subjected to the secondary intermediate grinding, 14 kg of isopropanol and 0.2 kg of a silane coupling agent A-1230 (Nihon Uniker Inc.) are respectively accommodated. Thereafter, these materials are subjected to the fine grinding treatment for 7 hours under conditions that a rotational speed is set to 1000 rpm and a vibration amplitude is set to 9 mm. The fine ground glass which is obtained through this stage is observed using an electron microscope and it is confirmed that at least 70 weight % or more of the fine ground glass exhibit a polyhedron having corners and faces.

v) Solid-Liquid Separation and Drying

The finely ground antimicrobial glass and isopropanol are subjected to solid-liquid separation using a centrifugal separator (made of Kokusan Inc.) under conditions of the rotational speed of 3000 rpm and 3 minutes). Subsequently, the antimicrobial glass is dried using an oven under conditions of a temperature of 105 degree centigrade and of 3 hours)

vi) Crushing

The antimicrobial glass which is dried and is partially formed into blocks is crushed using a geared crusher (made of Chuo Kakoki shoji Inc.) thus producing the antimicrobial glass (polyhedron glass). Here, the antimicrobial glass at this stage is observed using an electron microscope and it is confirmed that at least 90 weight % or more of the antimicrobial glass exhibits a polyhedron having corners and faces.

2. Evaluation of Antimicrobial Glass (1) Evaluation of Transparency

The transparency of obtained antimicrobial glass is judged based on following criteria using a microscope and a result of judgement is shown in Table 1.

Very good: no color and transparent
Good: partially non-transparent
Fair: whitening occurred partially
Bad: whitening occurred completely (2) Evaluation of Reflocculation The surface of the obtained antimicrobial glass (polyhedron glass) is judged based on following criteria using a microscope and a result of judgement is shown in Table 1.

Very good: substantially no fine antimicrobial glass deposited on periphery of antimicrobial glass
Good: slight deposition of fine antimicrobial glass on periphery of antimicrobial glass observed
Fair: some deposition of fine antimicrobial glass on periphery of antimicrobial glass observed
Bad: a large amount of deposition of fine antimicrobial glass on periphery of antimicrobial glass observed (3) Evaluation of Ag Ion Releasing Property 100 g of the obtained antimicrobial glass is immersed into 500 ml of distilled water (20 degree centigrade) and is subjected to shaking for 1 hour using a shaker. After separating an Ag ion released water using a centrifugal separator, the antimicrobial glass is filtered using a filter paper (5C) to produce a measuring sample. Ag ion in the measuring sample is measured based on the ICP emission spectroscopic analysis method and an Ag ion releasing amount (mg/kg conversion) is calculated. Here, ND in the Table shows that the Ag ion releasing amount is a value less than a detectable limit.

(4) Evaluation of Yellowing

To the obtained antimicrobial glass, ultraviolet rays (black panel temperature: 63 degree centigrade, illuminance 255 W/m$^2$ with light having a wavelength of 300 to 700 nm) are continuously irradiated using an ultraviolet ray irradiation device (made of Suga Shikenki Inc. Sunshine Weatherometer) and yellowing of the antimicrobial glass is judged based on the following criteria. The yellowing of the antimicrobial glass is measured using a microscope. A result of the measurement is shown in Table 1.

Very good: no color and transparent after lapse of 100 hours
Good: no color and transparent after lapse of 50 hours
Fair: no color and transparent after lapse of 10 hours
Bad: yellowing occurred after lapse of 10 hours (5) Evaluations of Antimicrobial Property 1 to 2

The obtained antimicrobial glass is mixed into a polypropylene resin such that the antimicrobial glass assumes 0.2 weight % so as to produce the resin containing the antimicrobial glass. Thereafter, a test piece containing the antimicrobial glass having a thickness of 2 mm, a longitudinal dimension of 5 cm and a lateral dimension of 5 cm is obtained by using a molding machine.

On the other hand, test bacteria is cultured in a agar planer medium made of Trypticase Soy Agar (BBL) at a temperature of 35 degree centigrade for 24 hours and, thereafter, a growth colony is suspended in an ordinary broth medium (made of Eiken Kagagu Inc.) having a concentration of 1/500 so as to adjust the growth colony to approximately $1 \times 10^6$ CFU/ml.

Subsequently, with the test piece containing the antimicrobial glass, 0.5 ml of a suspension of *Staphylococcus aureus* IFO#12732 and 0.5 ml of a suspension of *Escherichia coli* ATCC#8739 are uniformly brought into contact respectively. Further, a polyethylene-made film (sterilization) is placed on the suspensions and they are served as measuring samples in a film cover method.

Subsequently, measuring samples are placed in a thermostatic bath for 24 hours under conditions that a humidity is 95% and a temperature is 35 degree centigrade. Then, the number of funguses (growth colony) before test and the number of funguses (growth colony) after test are respectively measured and the antimicrobial property 1 (*Staphylococcus aureus* IFO#12732) and the antimicrobial property 2 (*Escherichia coli* ATCC#8739) are evaluated based on following criteria.

Here, the number of funguses (growth colony) before test is 2.6×10 (piece/test piece) with respect to both of Staphylococcus aureus IFO#12732 and Escherichia coli ATCC#8739. Results of respective tests are shown in table 1.

Very Good: the number of funguses after test being less than 1/10000 of the number of funguses before test
Good: the number of funguses after test being equal to or more than 1/10000 to less than 1/1000 of the number of funguses before test
Fair: the number of funguses after test being equal to or more than 1/1000 to less than 1/100 of the number of funguses before test
Bad: the number of funguses after test being equal to or more than 1/100 of the number of funguses before test Example 2

An antimicrobial glass having the similar glass composition (A composition) of the example 1 and formed of a polyhedron and having an average particle size of 10 μm is prepared and is evaluated. The obtained result is shown in Table 1.

Examples 3 to 5

An antimicrobial glass having the similar glass composition (A composition) of the example 1 and formed of a polyhedron and having an average particle size of 10 μm is prepared. Subsequently, in the fine grinding step, ZnO having an average particle size of 0.3 μm is added at addition amounts of 8 weight %, 2.7 weight % and 2.1 weight % respectively thus producing antimicrobial glasses containing externally deposited particles of the examples 3 to 5 and these glasses are evaluated. Obtained results are shown in Table 1.

Example 6

An antimicrobial glass containing externally deposited particles having an average particle size of 3 μm formed of a polyhedron in the same manner as the antimicrobial glass of the example is produced and evaluated except for followings. That is, the glass composition (B composition) is constituted such that, with respect to a total amount, the composition ratio of $P_2O_5$ assumes 59.6 weight %, the composition ratio of CaO assumes 26.3 weight %, the composition ratio of $Na_2O$ assumes 0.6 weight %, the composition ration of $B_2O_3$ assumes 10 weight %, the composition ratio of $Ag_2O$ assumes 3 weight %, and the composition ratio of $CeO_2$ assumes 0.5 weight %. Obtained results are shown in Table 2.

Examples 7 to 11

Antimicrobial glasses having the similar glass composition (B composition) as the example 6, formed of a polyhedron, and having an average particle size of 3 μm or 10 μm are prepared. Then, antimicrobial glasses containing externally deposited particles are prepared by setting an addition amount of ZnO having an average particle size of 0.3 μm to 2.5 weight %, 2.3 weight %, 1.2 weight % and 0 weight % respectively and are evaluated. Obtained results are shown in Table 2.

Examples 12 to 14

In the examples 12 to 14, antimicrobial glasses containing externally deposited particles are prepared and evaluated in the same manner as the antimicrobial glasses of the examples 3 to 5 except for that the externally deposited particles in the examples 3 to 5 are changed from ZnO having an average particle size of 0.3 μm to $SiO_2$ having an average particle size of 0.02 μm. Obtained results are shown in Table 3.

Examples 15 to 17

In the examples 15 to 17, antimicrobial glasses containing externally deposited particles are prepared and evaluated in the same manner as the antimicrobial glasses of the examples 8 to 10 except for that the externally deposited particles in the examples 8 to 10 are changed from ZnO having an average particle size of 0.3 μm to $Al_2O_3$ having an average particle size of 0.02 μm. Obtained results are shown in Table 3.

TABLE 1

| | example 1 | example 2 | example 3 | example 4 | example 5 |
|---|---|---|---|---|---|
| glass composition | A | A | A | A | A |
| $Ag_2O$ content (wt %) | 3 | 3 | 3 | 2 | 1 |
| average particle size (μm) | 3 | 10 | 10 | 10 | 10 |

TABLE 1-continued

|  | example 1 | example 2 | example 3 | example 4 | example 5 |
|---|---|---|---|---|---|
| externally deposited particles | none | none | ZnO 8% | ZnO 2.7% | ZnO 2.1% |
| transparency | Very Good | Good | Very Good | Very Good | Very Good |
| reflocculating property | Good | Good | Very Good | Very Good | Very Good |
| Ag releasing amount (mg/Kg) | 4320 | 2360 | 3.2 | 1.3 | 1.8 |
| evaluation of yellowing 1 | Very Good | Very Good | Very Good | Very Good | Very Good |
| evaluation of yellowing 2 | Very Good | Very Good | Very Good | Very Good | Very Good |
| evaluation of antimicrobial property 1 | Very Good | Very Good | Very Good | Very Good | Very Good |
| evaluation of antimicrobial property 2 | Very Good | Very Good | Very Good | Very Good | Very Good |

TABLE 2

|  | example 6 | example 7 | example 8 | example 9 | example 10 | example 11 |
|---|---|---|---|---|---|---|
| glass composition | B | B | B | B | B | B |
| Ag$_2$O content (wt %) | 3 | 3 | 3 | 2 | 1 | 1 |
| average particle size ($\mu$m) | 3 | 3 | 10 | 10 | 10 | 10 |
| externally deposited particles | none | ZnO 2.5% | ZnO 2.3% | ZnO 1.2% | ZnO 0.6% | none |
| transparency | Very Good | Very Good | Very Good | Very Good | Very Good | Very Good |
| reflocculating property | Good | Very Good | Very Good | Very Good | Very Good | Very Good |
| Ag releasing amount (mg/Kg) | 1700 | 3.3 | 0.08 | ND | ND | 58.4 |
| evaluation of yellowing 1 | Very Good | Very Good | Very Good | Very Good | Very Good | Very Good |
| evaluation of yellowing 2 | Very Good | Very Good | Very Good | Very Good | Very Good | Very Good |
| evaluation of antimicrobial property 1 | Very Good | Very Good | Very Good | Very Good | Very Good | Very Good |
| evaluation of antimicrobial property 2 | Very Good | Very Good | Very Good | Very Good | Very Good | Very Good |

TABLE 3

|  | example 12 | example 13 | example 14 | example 15 | example 16 | example 17 |
|---|---|---|---|---|---|---|
| glass composition | A | A | A | B | B | B |
| Ag$_2$O content (wt %) | 3 | 2 | 1 | 3 | 2 | 1 |
| average particle size ($\mu$m) | 10 | 10 | 10 | 10 | 10 | 10 |
| externally deposited particles | SiO$_2$ 8% | SiO$_2$ 2.7% | SiO$_2$ 2.1% | Al$_2$O$_3$ 2.3% | Al$_2$O$_3$ 1.2% | Al$_2$O$_3$ 0.6% |
| transparency | Very Good | Very Good | Very Good | Very Good | Very Good | Very Good |
| reflocculating property | Very Good | Very Good | Very Good | Very Good | Very Good | Very Good |
| Ag releasing amount (mg/Kg) | 8.0 | 7.0 | 9.0 | ND | ND | 4.0 |
| evaluation of yellowing 1 | Very Good | Very Good | Very Good | Very Good | Very Good | Very Good |
| evaluation of yellowing 2 | Very Good | Very Good | Very Good | Very Good | Very Good | Very Good |
| evaluation of antimicrobial property 1 | Very Good | Very Good | Very Good | Very Good | Very Good | Very Good |
| evaluation of antimicrobial property 2 | Very Good | Very Good | Very Good | Very Good | Very Good | Very Good |

Comparative Examples 1 to 2

1. Preparation of Antimicrobial Glass

In comparative examples 1 to 2, antimicrobial glasses having the similar glass constitution as those of the example 1 are respectively prepared. In the comparative example 1, the fine grinding performed in the example 1 is not performed and the shape of the antimicrobial glass is partially formed into a polyhedron by performing only the coarse grinding and the intermediate grinding and an average particle size is adjusted to 700 $\mu$m using a sieve of 24 mesh. Further, in the comparative example 2, the intermediate grinding and the fine grinding performed in the example 1 are not performed and the shape of the antimicrobial glass is maintained in a granular shape or in a block shape without being formed in a polyhedron and an average particle size is adjusted to 300 $\mu$m using a sieve of 48 mesh.

2. Evaluation of Antimicrobial Glass

With respect to the antimicrobial glasses which are obtained in the comparison examples 1 and 2 under the similar evaluation conditions as those of the example 1, transparency and the like thereof are evaluated respectively. A result of evaluation is shown in Table 4. However, with respect to the reflocculating property, since the antimicrobial glass of the comparative example 2 has the granular shape so that fine pieces of fine antimicrobial glass are not produced, the reflocculating property thereof cannot be evaluated. As can be clearly understood from the result, in the comparative example 1, the obtained antimicrobial glass suffers from whitening and lacks in transparency. This may be caused by the fact that the shape of the antimicrobial glass is not formed into a polyhedron and the average particle size is large. Further, yellowing caused by the irradiation of ultraviolet rays is partially observed. Further, it is also separately confirmed that dispersion and mixing of the antimicrobial glass into a resin is extremely difficult. On the other hand, with respect to the comparative example 2, although an average particle size is set to a value within a given range, the obtained antimicrobial glass suffers from whitening and lacks in transparency and also yellowing caused by the irradiation of ultraviolet rays is partially observed because of the fact that the shape of the antimicrobial glass is not formed in a polyhedron. Still further, it is confirmed that the dispersion and mixing of the antimicrobial glass into a resin is difficult.

TABLE 4

|  | comparative example 1 | comparative example 2 |
|---|---|---|
| glass composition | A | A |
| configuration | Polyhedron | Granular shape |
| average particle size (μm) | 700 | 300 |
| externally deposited particles | None | none |
| transparency | x | Fair |
| reflocculating property | Very Good | no evaluation |
| Ag releasing amount (mg/Kg) | 780 | 990 |
| evaluation of yellowing 1 | Fair | Fair |
| evaluation of antimicrobial property 1 | Good | Good |
| evaluation of antimicrobial property 2 | Fair | Fair |

INDUSTRIAL APPLICABILITY

As has been explained heretofore, according to the antimicrobial glass of the first embodiment, the shape of the antimicrobial glass is formed into a polyhedron and the average particle size is set to a value within a given range, and further, the antimicrobial glass has a given glass composition. Accordingly, yellowing of the antimicrobial glass can be reduced so that it is possible to provide the antimicrobial glass which exhibits excellent dispersing ability into a resin and the excellent transparency.

Further, according to the antimicrobial glass of the second embodiment, the shape of the antimicrobial glass is formed into a polyhedron and the average particle size is set to a value within a given range, and further, the antimicrobial glass has a given glass composition. Accordingly, yellowing of the antimicrobial glass can be reduced so that it is possible to provide the antimicrobial glass which exhibits the excellent dispersing ability into a resin and the excellent transparency.

Further, according to the antimicrobial glass of the third embodiment, the shape of the antimicrobial glass is formed into a polyhedron and the average particle size is set to a value within a given range, and further, the antimicrobial glass contains the externally deposited particles. Accordingly, it is possible to provide the antimicrobial glass which exhibits excellent dispersing ability into a resin and the excellent transparency and, at the same time, it is possible to prevent the reflocculation so that the Ag ion releasing property can be easily controlled.

Further, according to the antimicrobial glass of the fourth embodiment, the shape of the antimicrobial glass is formed into a polyhedron and the average particle size is set to a value within a given range, and further, the antimicrobial glass is subjected to the coupling agent treatment. Accordingly, it is possible to provide the antimicrobial glass which exhibits excellent dispersing ability into a resin and the excellent transparency and, at the same time, it is possible to prevent the reflocculation so that, when the antimicrobial glass is added into a resin, the antimicrobial glass can obtain the excellent adhesiveness.

Further, by mixing at least one of the antimicrobial glasses according to the first to fourth embodiments into a resin thus forming the antimicrobial resin compound and, thereafter, by molding the antimicrobial resin compound into the resin molded product of the fifth embodiment, the resin molded product can obtain the excellent surface flatness and the molded product can exhibit a desired color.

Still further, according to the manufacturing method of the antimicrobial glass in the sixth embodiment, yellowing can be reduced so that it is possible to efficiently provide the antimicrobial glass which exhibits the excellent dispersing ability to the resin and the excellent transparency.

What is claimed is:

1. An antimicrobial glass capable of releasing an Ag ion being characterized in that a shape of the antimicrobial glass is a polyhedron shape and an average particle size of the antimicrobial glass is set to a value within a range of 0.1 to 300 μm.

2. The antimicrobial glass according to claim 1, wherein the antimicrobial glass contains $Ag_2O$, $ZnO$, $CaO$, $B_2O_3$ and $P_2O_5$ as glass composition, and assuming a total amount as 100 weight %, a content of $Ag_2O$ is set to a value within a range of 0.2 to 5 weight %, a content of $ZnO$ is set to a value within a range of 1 to 50 weight %, a content of $CaO$ is set to a value within a range of 0.1 to 15 weight %, a content of $B_2O_3$ is set to a value within a range of 0.1 to 15 weight % and a content of $P_2O_5$ is set to a value within a range of 30 to 80 weight %, and a weight ratio of $ZnO/CaO$ is set to a value within a range of 1.1 to 15.

3. The antimicrobial glass according to claim 1, wherein the antimicrobial glass contains $Ag_2O$, $CaO$, $B_2O_3$ and $P_2O_5$ as glass composition provided that $ZnO$ is not substantially contained, and assuming a total amount as 100 weight %, a content of $Ag_2O$ is set to a value within a range of 0.2 to 5 weight %, a content of $CaO$ is set to a value within a range of 15 to 50 weight %, a content of $B_2O_3$ is set to a value within a range of 0.1 to 15 weight % and a content of $P_2O_5$ is set to a value within a range of 30 to 80 weight %, and a weight ratio of $CaO/Ag_2O$ is set to a value within a range of 5 to 15.

4. The antimicrobial glass according to claim 1, wherein externally deposited particles having an average particle size of 0.01 to 100 μm and having an average particle size smaller than the average particle size of the antimicrobial glass are added.

5. An antimicrobial glass according to claim 1, wherein a coupling agent treatment is applied to a surface of the antimicrobial glass.

6. A method for producing an antimicrobial glass formed of polyhedron-shaped antimicrobial glass being characterized by comprising following steps (A) to (C);

(A) a step in which glass materials containing at least $Ag_2O$ is melted thus forming a glass melt, (B) a first grinding step in which the glass melt is formed into a coarsely ground glass having an average particle size which exceeds 300 μm, and (C) a second grinding step in which the coarsely ground glass is formed into a polyhedron glass having an average particle size which is a value within a range of 0.1 to 300 μm.

7. A method for producing an antimicrobial glass according to claim 6, wherein a rotary mill, rotary rollers, a vibration mill, a ball mill, a sand mill or a jet mill is used in the step (C).

8. A method for producing an antimicrobial glass according to claim 6, wherein the method further includes a following step (D) before or after or in the step (C).

(D) a step in which externally deposited particles having an average particle size which is a value within a range of 0.01 to 100 μm and is smaller than an average particle size of the antimicrobial glass are added.

9. A method for producing an antimicrobial glass according to claim 6, wherein the method further includes a following step (D) before or after or in the step (C), (D) a step in which coupling agent treatment is applied to a surface of the coarsely ground glass.

10. An antimicrobial glass according to claim 2, wherein externally deposited particles having an average particle size of 0.01 to 100 μm and having an average particle size smaller than the average particle size of the anti microbial glass are added.

11. An antimicrobial glass according to claim 3, wherein extremely deposited particles having an average particle size of 0.01 to 100 μm and having an average particle size smaller than the average particle size of the anti microbial glass are added.

12. An antimicrobial glass according to claim 2, wherein a coupling agent treatment is applied to a surface of the antimicrobial glass.

13. An antimicrobial glass according to claim 3, wherein a coupling agent treatment is applied to a surface of the antimicrobial glass.

14. An antimicrobial glass according to claim 4, wherein a coupling agent treatment is applied to a surface of the antimicrobial glass.

15. An antimicrobial glass according to claim 10, wherein a coupling agent treatment is applied to a surface of the antimicrobial glass.

16. An antimicrobial glass according to claim 11, wherein a coupling agent treatment is applied to a surface of the antimicrobial glass.

17. A method for producing an antimicrobial glass according to claim 7, wherein the method further includes a following step (D) after step (C):

(D) a step in which externally deposited particles having an average particle size which is a value within a range of 0.01 to 100 μm and is smaller than an average particle size of the antimicrobial glass are added.

18. A method for producing an antimicrobial glass according to claim 7, wherein the method further includes a following step (D) after the step (C):

(D) a step in which coupling agent treatment is applied to a surface of the coarsely ground glass.

19. A method for producing an antimicrobial glass according to claim 8, wherein the method further includes a following step (E) after the step (D):

(E) a step in which coupling agent treatment is applied to a surface of the coarsely ground glass.

20. A method for producing an antimicrobial glass according to claim 17, wherein the method further includes a following step (E) after the step (D):

(E) a step in which coupling agent treatment is applied to a surface of the coarsely ground glass.

* * * * *